US005215530A

United States Patent [19]

Hogan

[11] Patent Number: 5,215,530
[45] Date of Patent: Jun. 1, 1993

[54] SLEEVED EXTENSION AND ANCHORING SYSTEM FOR PERCUTANEOUS CATHETERS

[75] Inventor: J. Martin Hogan, Long Beach, Calif.

[73] Assignee: City of Hope, Duarte, Calif.

[21] Appl. No.: 728,721

[22] Filed: Jul. 11, 1991

[51] Int. Cl.⁵ .................. A61M 5/32; A61M 31/00
[52] U.S. Cl. .................... 604/174; 604/175; 604/53
[58] Field of Search ........... 604/174, 175, 164, 178, 604/93, 280, 891.1

[56] References Cited

U.S. PATENT DOCUMENTS

| 4,676,782 | 6/1987 | Yamamoto et al. | 604/175 |
| 4,863,426 | 9/1989 | Ferragamo et al. | 604/175 |
| 4,869,719 | 9/1989 | Hogan | 604/174 |
| 4,936,826 | 6/1990 | Amarasinghe | 604/175 |
| 5,041,085 | 8/1991 | Osborne et al. | 604/178 |
| 5,078,689 | 1/1992 | Keller | 604/174 X |

FOREIGN PATENT DOCUMENTS 2057269 4/1981 United Kingdom ............... 604/174

Primary Examiner—Gene Mancene
Assistant Examiner—Nicholas D. Lucchesi
Attorney, Agent, or Firm—Edward S. Irons

[57] ABSTRACT

A catheter apparatus having a percutaneous catheter with lengths of sleeved tubing fitted over the percutaneous catheter tube external to a patient with a bushing abutting against a retaining plate which are used to retain the percutaneous catheter adjacent the patient's skin.

11 Claims, 8 Drawing Sheets

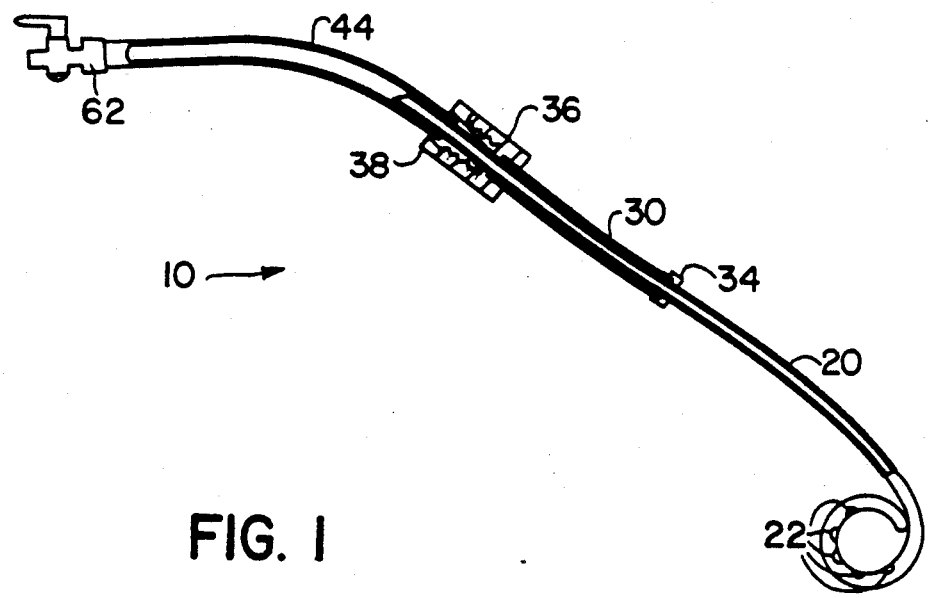
FIG. 1
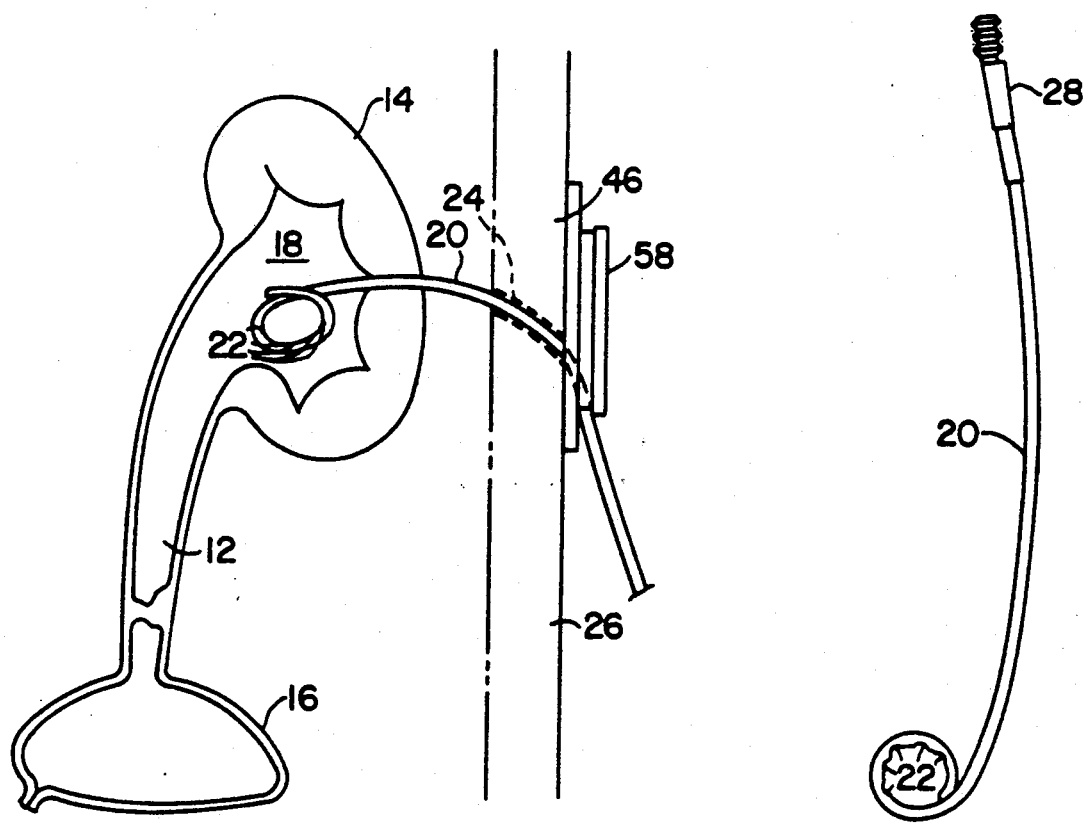
FIG. 2
FIG. 3

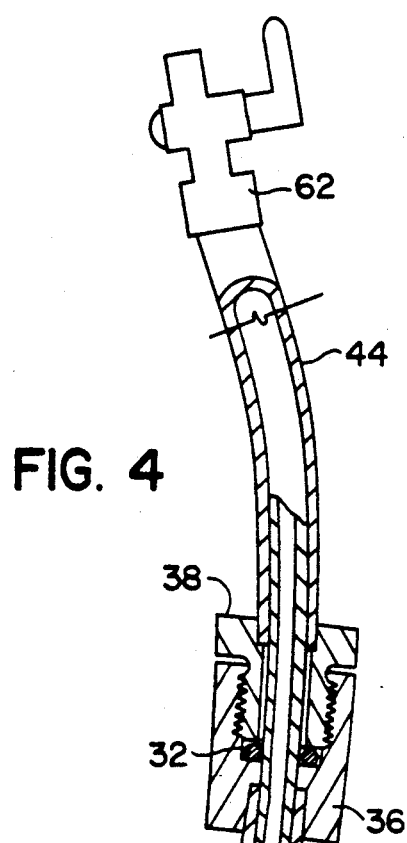
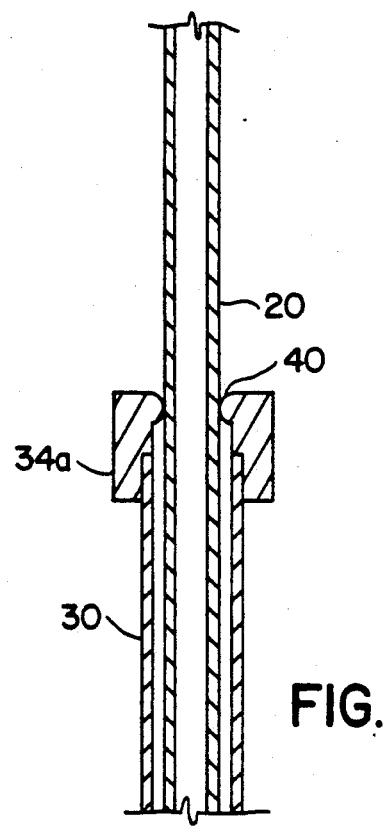
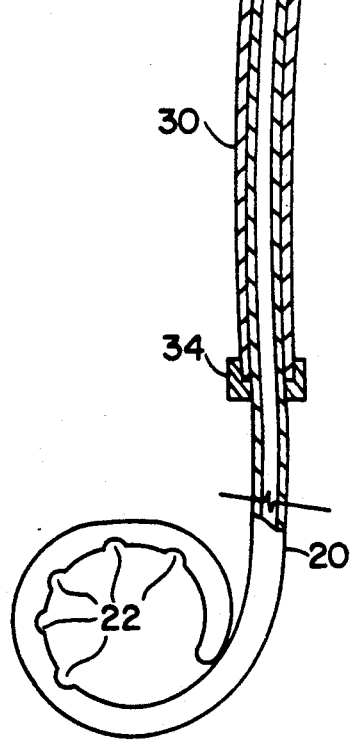
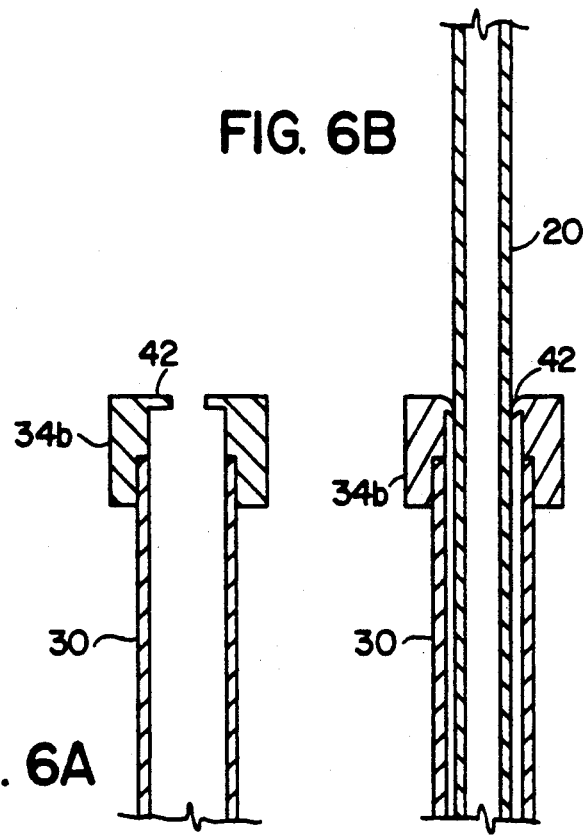
FIG. 4
FIG. 5
FIG. 6A
FIG. 6B

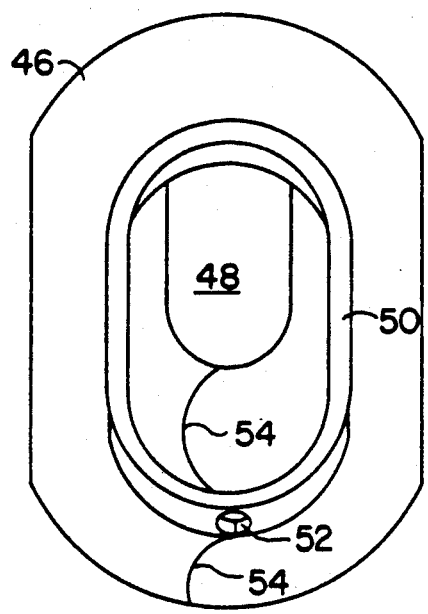
FIG. 11
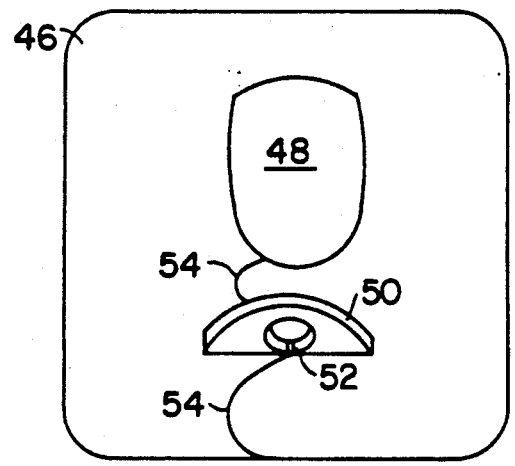
FIG. 12
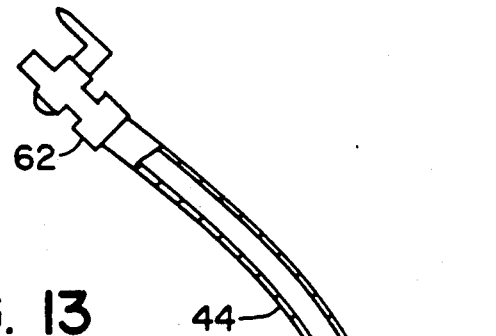
FIG. 13
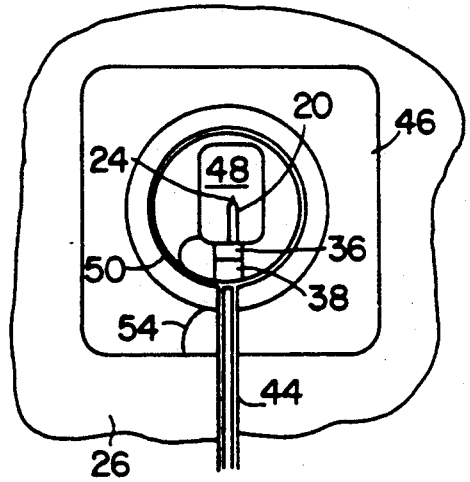
FIG. 14
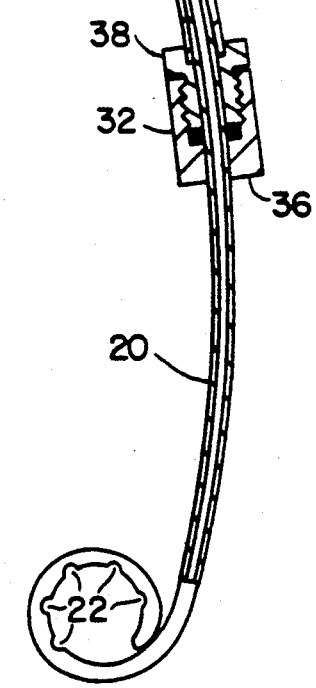

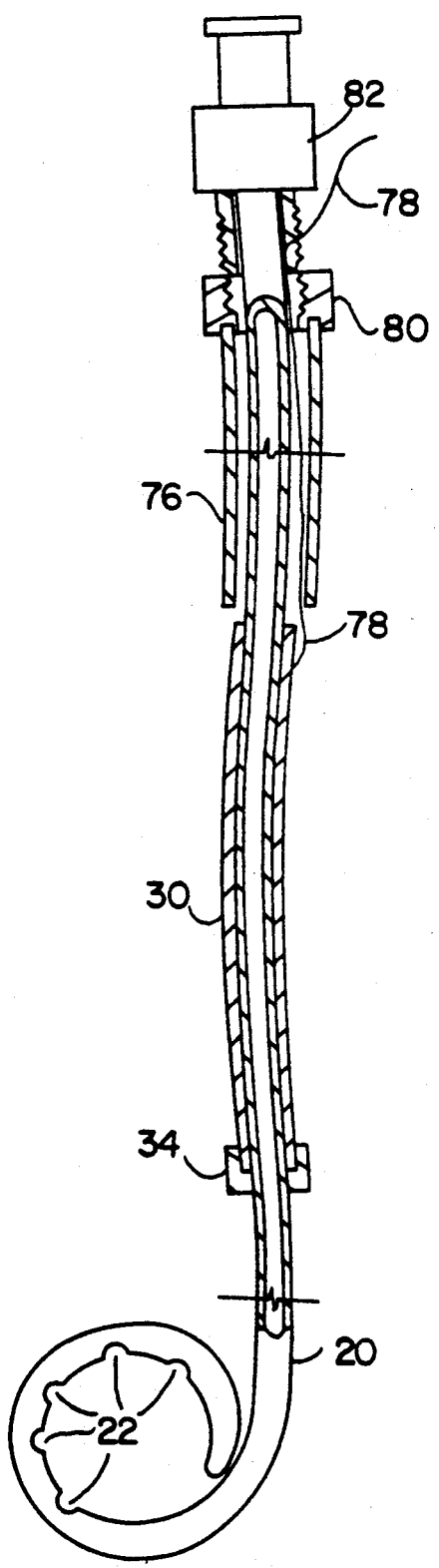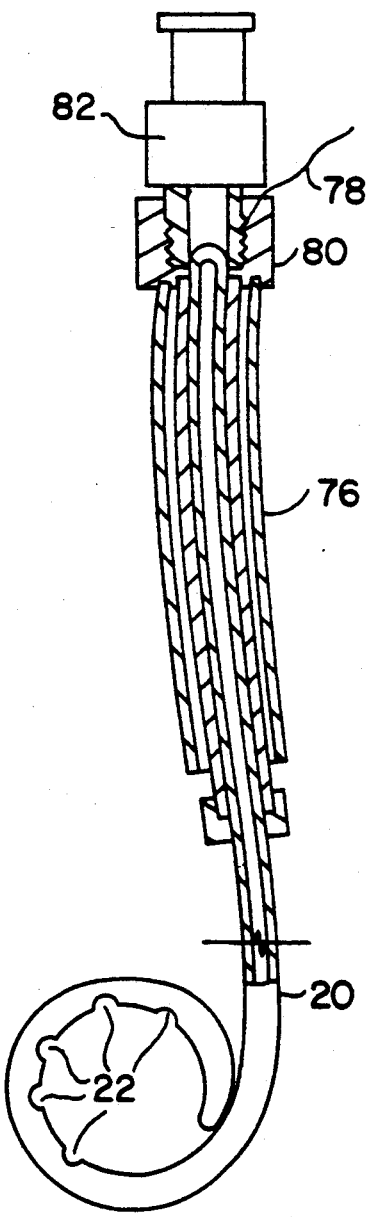
FIG. 18
FIG. 19

SLEEVED EXTENSION AND ANCHORING SYSTEM FOR PERCUTANEOUS CATHETERS

TECHNICAL FIELD

The present invention relates generally to a sleeving system for extending and anchoring percutaneous catheters, and more specifically to a sleeving system that can both be used as part of insertion of a percutaneous catheter in a patient, or can be used to repair damaged percutaneous catheters that were previously inserted in patients.

BACKGROUND ART

Use of percutaneous catheters to drain fluids from or inject fluids into a patient is known and is a well-accepted method for medical treatment. For example, when the passage between a kidney and the bladder is blocked, accepted treatment can be provided by catheterization of the kidney to drain urine. Catheterization involves initially using needles to insert a percutaneous catheter into the kidney with the blocked passage. The distal end of the inserted percutaneous catheter includes multiple openings for passing fluid to or from the percutaneous catheter. Retention of inserted percutaneous catheters in organs is facilitated by having the distal end of percutaneous catheters pre-stressed for formation of loops (e.g., see U.S. Pat. No. 4,419,094).

At locations where percutaneous catheters exit patients' bodies, anchoring to the skin of the percutaneous catheters can be provided by plastic plates held against the skin with adhesives while the percutaneous catheters are separately joined to the plates (e.g., see again U.S. Pat. No. 4,419,094). Known plastic plates for anchoring percutaneous catheter tubes to a patient's skin have included radial slits from the outer edge of the plates to the locations where the percutaneous catheters pass through the plates. The slits facilitate positioning of percutaneous catheters through the plates without having to be threaded through holes in the plates. Clamps have been used to join percutaneous catheters to plates. Alternatively, set screws have been used to fix the position of percutaneous catheters to plates. These previously known plates for anchoring percutaneous catheters have also included chambers in which gauze can be positioned about the percutaneous catheters at locations of entry to patients' bodies (e.g., see U.S. Pat. No. 4,516,968).

Systems for both anchoring percutaneous catheters to skin and for adjusting the length of percutaneous catheters in patients' bodies are also previously known (e.g., see U.S. Pat. No. 4,869,719).

The above known catheter systems and anchoring mechanisms for catheters fail to lend themselves to convenient repair when an external section or sections of an inserted percutaneous catheter is damaged. Damage of interest here defeats the purpose of an inserted percutaneous catheter. In addition to ruptured tube wall damage there is kinking damage which blocks passage of fluid through an inserted percutaneous catheter.

DISCLOSURE OF INVENTION

Insertion of percutaneous catheters in patients involves unavoidable risks and usually is intended for use over extended periods of time. With use over extended periods of time, the probability of damage to external sections of inserted percutaneous catheters increases. A patient's mobility can further increase the probability of damage to the external section of inserted percutaneous catheters. A common cause of damage to external sections of inserted percutaneous catheters is kinking.

In order to facilitate insertion of percutaneous catheters in patients and to assure retention of the original cylindrical shape when external pressures are applied to percutaneous catheters the material from which these percutaneous catheters are made needs to have the characteristics of both elasticity and stiffness. The material, in other words, needs to be stiff and spring like as opposed to supple. These characteristics unavoidably facilitate kinking when a section of external percutaneous catheter is bent at sharp angles. The resulting kinking unavoidably causes a crease with decreased cross-sectional area of the internal lumen, which restricts fluid flow through that section of the percutaneous catheter.

When an inserted percutaneous catheter is damaged, the least acceptable action is to remove the percutaneous catheter and insert a new one. Reasons for wanting to avoid such action includes the possibility of causing unintended injury to the patient in removing and inserting percutaneous catheters. Further, removal and insertion of a new percutaneous catheter increases the probability of causing infection.

It is an object of the present invention to provide a system that can be used with a previously inserted percutaneous catheter to repair damaged external lengths of the percutaneous catheter. Such repair is provided by permitting the percutaneous catheter to be cut so damaged sections can be removed and the apparatus of the present invention can be joined to the remaining inserted percutaneous catheter to permit insertion or drainage of fluids from a patient and to further provide for anchoring of the inserted percutaneous catheter to the patient's skin.

Another object of the present invention is to provide a system where a percutaneous catheter can be inserted in a patient and the external length of the inserted percutaneous catheter can be minimized so as to preclude the possibility of kinking. Joined to the external length of percutaneous catheter is tubing of the present invention. Specifically, tubing of the present invention beyond the inserted percutaneous catheter can be made of supple material which can be bent at sharp angles without causing permanent kinking. In other words, after subjecting external sections of tubing of the present invention to sharp angles, the tubing internal cross-sectional area returns approximately to the same size as before the bending so fluid flow is not restricted.

BRIEF DESCRIPTION OF THE DRAWINGS

Various objects, advantages and novel features of the present invention will become more readily apprehended from the following detailed description when taken in conjunction with the appended drawings in which:

FIG. 1 is a plan partial sectional view of the catheter apparatus of a first embodiment of the present invention including a section of percutaneous catheter tubing;

FIG. 2 is a schematic view of a patient's kidney and bladder showing an inserted percutaneous catheter from the kidney to the patient's skin and a retaining plate adhered to a patient's skin for fixing the position of the inserted percutaneous catheter;

FIG. 3 is a plan view of a percutaneous catheter including a connection hub;

FIG. 4 is an enlarged plan partial sectional view of the percutaneous catheter system of the present invention showing use of both a distal sleeve and a proximal sleeve with a percutaneous catheter;

FIG. 5 is a sectional view of both a portion of a percutaneous catheter and a distal sleeve showing a connecting bushing with a flange arrangement for providing a fluid tight seal to the percutaneous catheter;

FIGS. 6A and 6B are partial sectional views of a connecting bushing for a distal sleeve showing use of a diaphragm for providing a fluid tight seal to a percutaneous catheter;

FIG. 11 is a plan view of an alternative configuration for a retaining plate useful with the present invention;

FIG. 12 is a plan view of another alternative configuration for a retaining plate useful with the present invention;

FIG. 13 is a plan partial sectional view of a second embodiment of a catheter apparatus according to the present invention;

FIG. 14 is a partial plan view of a retaining plate showing an inserted section of the catheter apparatus of the present invention;

FIG. 18 is a plan partial sectional view of a fifth embodiment of the catheter apparatus of the present invention showing use of telescoping tubing with the tubes extended;

FIG. 19 is a plan partial sectional view of the fifth embodiment of the catheter apparatus of the present invention showing use of telescoping tubing with the tubes slid over each other;

BEST MODE FOR CARRYING OUT THE INVENTION

Figure 7:
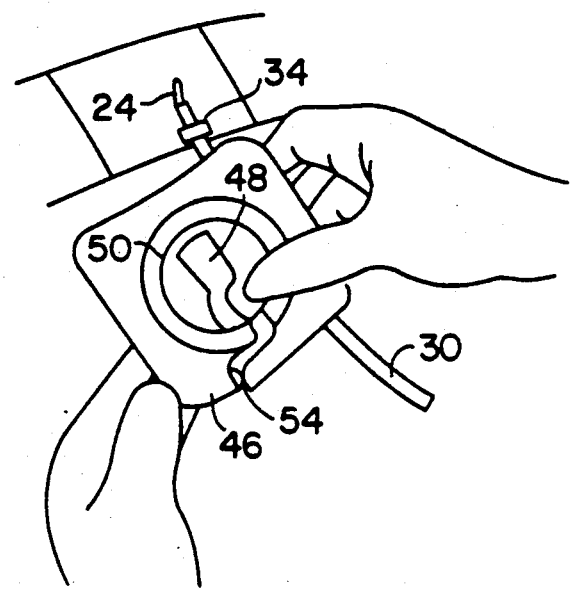
FIG. 7 is a perspective view of a retaining plate showing positioning of a percutaneous catheter apparatus of the present invention in the retaining plate.

A first embodiment for a catheter apparatus according to the present invention is shown in FIG. 1 where it is generally designated by reference numeral 10.

Utilization of the catheter apparatus 10 of the present invention is described below in conjunction with draining urine from kidneys. The catheter apparatus 10 of the present invention is not intended only for draining urine from kidneys or for that matter fluid draining exclusively. Instead urine drainage was selected as being generally descriptive of many types of medical procedures where the catheter apparatus 10 of the present invention could be used. Such usage can include all types of fluid drainage and can also include fluid injection.

Turning for illustrative purposes to fluid drainage from kidneys, when the ureter 12 from a kidney 14 to the bladder 16 is blocked urine will accumulate in the hollow interior 18 of the kidney 14 (see FIG. 2). To drain accumulated urine, catheter apparatus 10 can be used with a percutaneous catheter 20 (see FIG. 3) inserted in the kidney 14 having the blocked ureter 12. The percutaneous catheter 20 is known and can be made of plastic and can be of such sizes as 8.3, 10 or 12 French catheters. At the proximal end of the percutaneous catheter 20 there are multiple passages 22 through the percutaneous catheter 20 permitting fluid flow into or out of the percutaneous catheter 20. Stressed prior to insertion into the patient the proximal end or tip end of the percutaneous catheter 20 assumes a loop shape to facilitate retention in the hollow interior 18 of the kidney 14 (see FIG. 2). In the alternative the tip end of the percutaneous catheter 20 may be made straight or made with curve. Insertion of the percutaneous catheter 20 into a patient is through a tiny incision or puncture 24 at the skin 26 entry site.

The percutaneous catheter 20 can be inserted in a kidney 14 in a manner well known in the art. For example, a needle (not shown) with a sheath (not shown) can be inserted into the hollow space 18 of the kidney 14 through a tiny incision 24 at the skin 26 entry site. The needle is then withdrawn but the sheath is retained in position from the incision 24 to the hollow space 18 in the kidney 14. A flexible metal guide wire (not shown) is then inserted through the sheath. After the guide wire is passed through the sheath, the sheath is withdrawn, leaving the guide wire positioned from the incision 24 to the hollow space 18 in the kidney 14.

Tubings of progressively larger diameters are passed along the length of the guide wire to expand the diameter of the passage through the patient between the incision 24 and the hollow space 18 in the kidney 14. After each tube is passed over the guide wire, it is withdrawn before the next tube of increased diameter is passed over the guide wire. Finally the percutaneous catheter 20 is passed into the hollow space 18 of the kidney 14 and the guide wire is removed from the patient.

An advantage of the catheter apparatus 10 of the present invention is its adaptability for use either during initial insertion of the percutaneous catheter 20 in a patient or as a kit for repairing previously inserted percutaneous catheters that have been damaged by, for example, rupture or kinking. As will be clear the following discussion is applicable to either use of the present invention during initial insertion of a percutaneous catheter 20 or as a repair kit for a damaged previously inserted percutaneous catheter 20.

With the percutaneous catheter 20 inserted in the patient the percutaneous catheter hub 28 is cut off. Then a distal sleeve 30 and a washer 32 sized to snugly fit on the percutaneous catheter tube 20 are advanced down the percutaneous catheter tube 20 until the distal sleeve bushing 34 is adjacent the entry point of the percutaneous catheter tube 20 into the patient.

The relationship of the outside diameter of the percutaneous catheter 20 to the inside diameter of the distal sleeve 30 can be selected so as to provide a close fit which is loose enough to permit sliding of the distal sleeve 30 over the percutaneous catheter 20. Tolerances for this fit cannot be s tight as to result in unacceptably high friction in sliding the distal sleeve 30 over the percutaneous catheter 20. Facilitating such a fit is the fact that a fluid tight seal with the percutaneous catheter 20 is provided by the washer 32 when compressed by the joined female threaded distal sleeve hub 36 and the male threaded proximal sleeve hub 38 (see, FIG. 4). Therefore, it is not a close fit between the distal sleeve 30 and the percutaneous catheter 20 that provides the required fluid tight seal to the percutaneous catheter 20.

To even further reduce the possibility of difficulty in sliding the distal sleeve 30 over the percutaneous catheter 20, the inside diameter of the distal sleeve 30 can be substantially increased so there no longer is a close fit between the two. In this situation advantages from having a close fit between the percutaneous catheter 20 and the distal sleeve 30 are lost. Resulting disadvantages can include not having some friction between the distal sleeve 30 and the percutaneous catheter 20 to facilitate handling of the two during assembly, and also difficulty in maintaining centering of the percutaneous catheter 20 in the distal sleeve 30. Alternative bushing 34a and 34b designs are provided by the present invention to overcome these problems. One of these designs is shown in FIG. 5 as an alternative bushing 34a that includes a flange 40. The flange 40 is so dimensioned as to provide a close fit against the outside of the percutaneous catheter 20, but again this close fit is not so tight as to cause difficulty by excessive friction in sliding the distal sleeve 30 over the percutaneous catheter 20. Another design is shown in FIGS. 6A and 6B as an alternative bushing 34b that includes a diaphragm 42. The diameter of the opening in the diaphragm 42 is dimensioned so when a percutaneous catheter 20 is inserted into the distal sleeve 30 the diaphragm 42 is deflected into the lumen of the distal sleeve 30 and provides a seal to the percutaneous catheter 20. Again the diameter of the opening in the diaphragm 42 is dimensioned so as to provide a close fit against the outside of the percutaneous catheter 20 but not so tight a fit as to cause difficulty, by excessive friction, in sliding the distal sleeve 30 over the percutaneous catheter 20. A capability provided by the bushing 34b design with the diaphragm 42 is the fact that different sizes of percutaneous catheters 20 can be accommodated. This capability is achievable without encountering excessive friction because use of a diaphragm design permits differing flexure of diaphragm 42 walls into the distal sleeve 30 lumen depending on the diameter of the percutaneous catheter 20.

Further assembly of the catheter apparatus 10 of the present invention can require a second cutting of the percutaneous catheter 20 so three to four inches of the percutaneous catheter 20 extends beyond the end of the female threaded distal sleeve hub 36 after the distal sleeve 30 is slid over the percutaneous catheter 20 and the distal sleeve bushing 34 is positioned adjacent incision 24. Washer 32, male threaded proximal sleeve hub 38 and proximal sleeve 44 are now slide over the section of percutaneous catheter 20 extending beyond the female threaded distal sleeve hub 36. The male threaded proximal sleeve hub 38 is now joined to the female threaded distal sleeve hub 36 with washer 32 accordingly compressed to provide a fluid tight seal about the percutaneous catheter 20. It is noted the washer 32 is not the retention mechanism for retaining the position of the percutaneous catheter 20 within the body space or organ.

Figure 8:
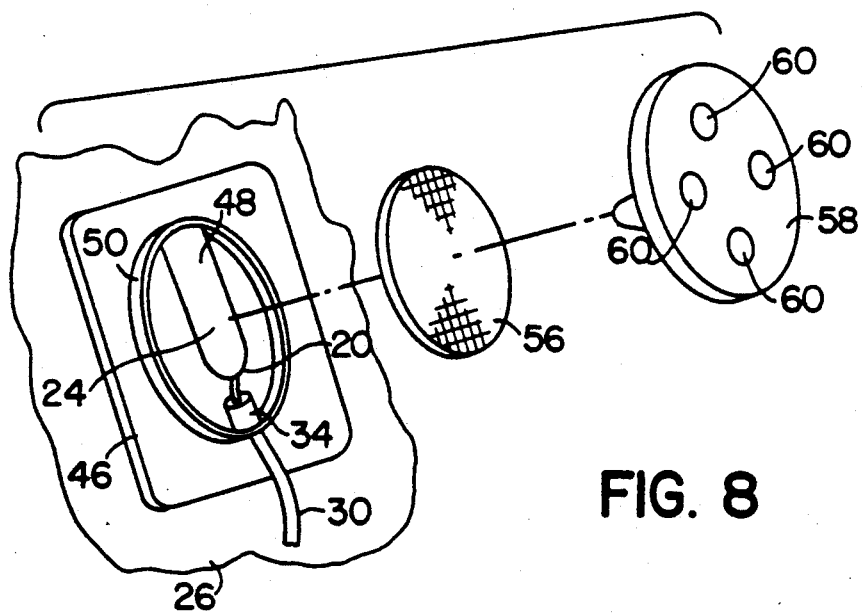
FIG. 8 is an exploded perspective view of a retaining plate adhered to a patient's skin that can be used with the present invention.
Figure 9A:
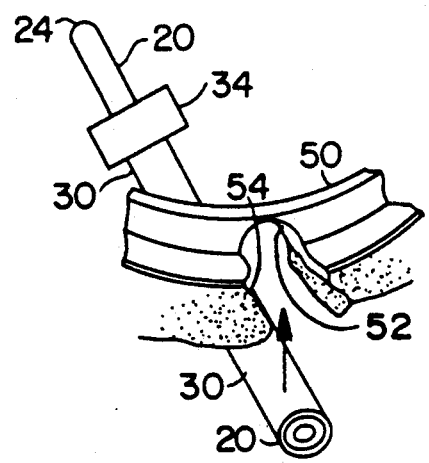
FIG. 9A is a perspective view showing a partial view of a percutaneous catheter apparatus of the present invention being positioned in an aperture located in a rim of a retaining plate.
Figure 9B:
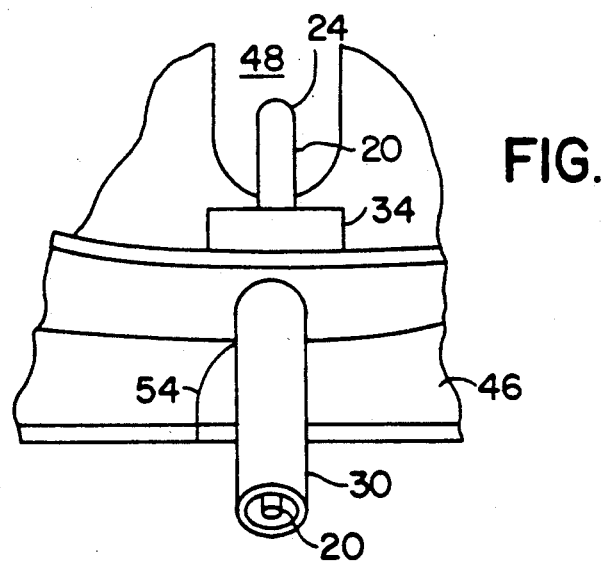
FIG. 9B is a perspective view showing a partial view of a percutaneous catheter apparatus of the present invention positioned in an aperture located in a rim of a retaining plate.
Figure 10:
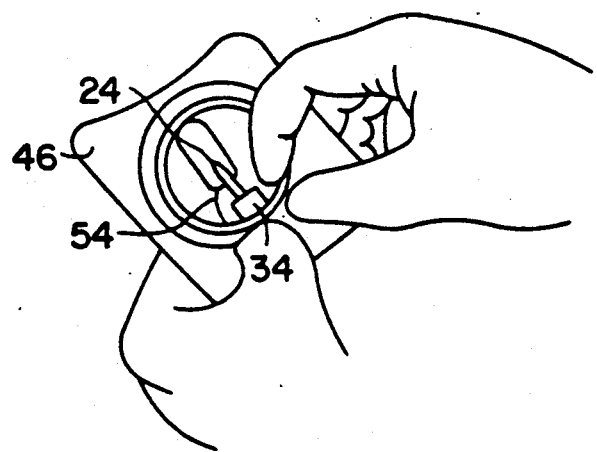
FIG. 10 is another perspective view of a retaining plate showing positioning of the catheter apparatus of the present invention in the retaining plate.

A retaining plate 46 with an adhesive backing is now applied to the patient and catheter apparatus 10 of the present invention as shown in FIG. 7. A wafer plate with an adhesive backing that can be modified, as described below, for use as retaining plate 46 is sold by Squibb under the trademark STOMAHESIVE. The retaining plate 46 includes a central plate opening 48 and is positioned on a patient's skin 26 so the catheter skin entry site 24 is centered in the plate opening 48 (see FIG. 8). A rim 50 extends from the surface of the retaining plate 46 and away from the patient's skin 26. This rim 50 includes a rim aperture 52 by which the distal sleeve bushing 34 is to be retained (see FIGS. 8, 9 and 10). Positioning the distal sleeve bushing 34 against the medial or inside face of rim aperture 52 is facilitated by providing a cut 54 in retaining plate 46. Specifically the cut 54 allows temporary opening of the plate 46 and the aperture 52 along the cut 54 to permit positioning the distal sleeve 30 with the encased percutaneous catheter 20 into the plate opening 48 and the distal sleeve 30 into the rim opening 52, and permits the distal sleeve bushing 34 to be positioned against the inside face of rim aperture 52.

Once the sleeve 30 and the retention bushing 34 are thus positioned, the cut 54 and the rim aperture 52 are again closed allowing the edges of the plate 46 along cut 54 to again oppose one another. The closed rim aperture 52 now closely fits the sleeve 30 and the retention bushing 34 cannot be pulled through the closed rim aperture 52 by forces applied to catheter apparatus 10 external to rim 50.

The retaining plate 46 is next adhered to the patient's skin 26. Thus affixed to the skin 26, the percutaneous catheter 20 is protected from unintentional removal from a patient by forces applied to the catheter apparatus 10 external to the rim 50.

With the retaining plate 46 adhered to a patients' skin 26 and the distal sleeve bushing 34 mounted against the inside face of the rim opening 52 a gauze pad 56 can be positioned in the volume defined by retaining plate 46 and rim 50. Then a cover 58 having openings 60 can be positioned over opening 48 and gauze pad 56, if it is used, and the cover 58 can be retained at that location by a press fit with rim 50. The gauze pad 56 absorbs fluids coming from incision 24, and helps keep catheter entry site 24 clean, and also assists in restraining movement of percutaneous catheter 20 with respect to retaining plate 46. Openings 60 in cover 58 permit visual inspection of gauze pad 56 and aeration of catheter entry site 24.

Alternative designs for retaining plate 46 as shown in FIGS. 7, 8, 10 and 13, are shown in FIGS. 11 and 12. These alternative retaining plate 46 designs center on the configuration for the rim 50. For example, rim 50 can be other than circular in layout, as shown in FIG.

11 where it is oval. Other layouts for continuous closed rims 50 are also acceptable. In point of fact, there is not a requirement for having rim 50 be in a continuous closed layout. A segmental rim 50 configuration is shown in FIG. 12. Important specifications for retaining plate 46 are that the combination with the cut 54 permit sufficient opening before application to a patient of the retaining plate 46 that the distal sleeve 30 with the encased percutaneous catheter 20 can be properly positioned in the retaining plate 46. Proper positioning requires that when the cut 54 is closed the rim aperture 52 snugly fit about the distal sleeve 30 so the distal sleeve bushing 34 not be able to migrate through the rim aperture 52. Either embodiment for retaining plate 46, as shown in FIGS. 11 and 12, or other useful variations of these embodiments can be directly used with the present invention as described and their substitution for the retaining plate 46 embodiment shown in at least FIGS. 7, 8, 10 and 13 is within the scope of the present invention.

Forces applied to the distal sleeve 30 and proximal sleeve 44 are not exclusively coupled to the percutaneous catheter 20 because there is a coupling of forces to the retaining plate 46 via the distal sleeve bushing 3 which is fixed to the retaining plate rim 50. Such arrangement contributes to assuring the percutaneous catheter 20 is not unintentionally removed from a patient.

Significantly contributing to advantages achieved with the catheter apparatus 10 of the present invention is the extension of the percutaneous catheter 20 in the proximal sleeve 44 beyond the male threaded proximal sleeve hub 38. Further the distal sleeve 30 and proximal sleeve 44 are preferably made of supple material which is not susceptible to kinking. Finally a connection mechanism such as a stopcock 62 is provided at the end of the proximal sleeve 44 for faciliatating connection to the remainder of the system used for catheterization.

A second embodiment of the catheter apparatus 10 of the present invention uses only a proximal sleeve 44 instead of both a distal sleeve 30 and a proximal sleeve 44 in combination with a percutaneous catheter 20 (see, FIG. 13). As with the first embodiment the proximal sleeve 44 here is fitted to a male threaded sleeve hub 38 but the proximal sleeve 44 is now fixed to the male threaded sleeve hub 38 prior to being joined with the percutaneous catheter 20. A matching female threaded sleeve hub 36 and washer 32 are also provided. Again as in the first embodiment the male threaded sleeve hub 38, female threaded sleeve hub 36 and washer 32 are sized to fit the selected percutaneous catheter 20 diameter, which can, [for example] typically, be any of 8.3, 10 or 12 French size catheters. The male threaded sleeve hub 38 and female threaded sleeve hub 36 may be sized to accept several different washer sizes, so that proximal sleeve 44 can accept several catheter sizes. This second embodiment can also be used either as the initial catheter insertion system or as a repair kit for an externally damaged catheter system.

Prior to placement of a percutaneous catheter 20 in a patient, according to the second embodiment, appropriately sized female threaded sleeve hub 36 and washer 32 are slid on the percutaneous catheter 20. Using standard techniques, such as described above, the percutaneous catheter is placed in a patient through catheter entry site 24. The female threaded sleeve hub 36 and washer 32 are then slid down the percutaneous catheter 20 proximal the catheter entry site 24 and about two inches beyond the washer 32 the percutaneous catheter 20 is cut off. Now the male threaded sleeve hub 38 with attached proximal sleeve 44 is slid on the percutaneous catheter 20. Note the male threaded sleeve hub 38 has a sufficiently large lumen as to allow the percutaneous catheter 20 to freely slide into the proximal sleeve 44 lumen. To complete the joining of the proximal sleeve 44 to the percutaneous catheter 20 the male threaded sleeve hub 38 and female threaded sleeve hub 36 are coupled. This coupling compresses the washer 32, thus forming a fluid tight seal about the percutaneous catheter 20. However, as with the first embodiment, compression of washer 32 is not increased beyond that necessary for providing a fluid tight seal. Other structure is used to prevent the percutaneous catheter 20 from pulling out of the proximal sleeve 44.

Alternative practice for this second embodiment, would be preassembly of proximal sleeve 44 with the male threaded sleeve hub 38 and female threaded sleeve hub 36 only loosely connected to include the washer 32. In this way, the preassembled proximal sleeve system could be mounted on a percutaneous catheter 20 positioned in a patient in one step. The male threaded sleeve hub 38 and female threaded sleeve hub 36 would then only require tightening to form a fluid tight seal about the percutaneous catheter 20.

With the percutaneous catheter 20 inserted in the patient and the proximal sleeve 44 mounted o the percutaneous catheter 20, a retaining plate 46 is positioned with the percutaneous catheter 20 in the plate opening 48 using the cut 54. So configured the retaining plate 46 is moved to have the male threaded sleeve hub 38 abut against rim 50 (see, FIG. 14) with the proximal sleeve 44 passed through rim aperture 52. Now the retaining plate 46 is adhered to the patient's skin 26, and the male threaded sleeve hub 38 abutting the rim 50 restrains withdrawal of the percutaneous catheter 20 from the patient.

Figure 15:
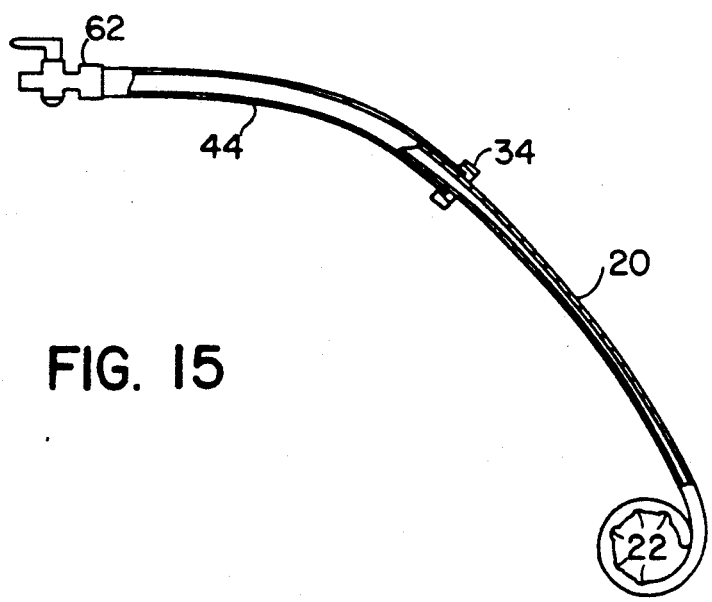
FIG. 15 is a plan partial sectional view of a third embodiment of a catheter apparatus according to the present invention.
Figure 16A:
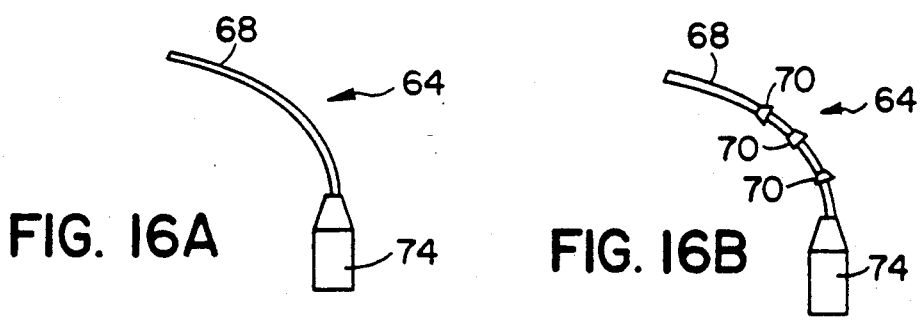
FIGS. 16A and 16B are plan views of curved blunt needles used with the catheter apparatus of the present invention as shown in FIG. 17.
Figure 16B:
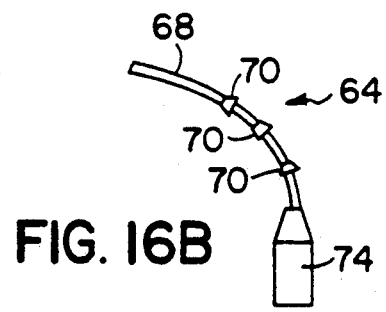

The third embodiment of the catheter apparatus 10 of the present invention also uses only a proximal sleeve 44 instead of both a distal sleeve 30 and proximal sleeve 44 with a percutaneous catheter 20 as does the first embodiment (see, FIG. 15) Unlike the first and second embodiment, the proximal sleeve 44 here is fitted with a bushing 34. As with the first two embodiments, this third embodiment can also be used either as the initial catheter retention system or as a repair kit for an externally damaged percutaneous catheter.

Using standard techniques, such as described above, a percutaneous catheter 20 is placed in a patient through an catheter entry site 24. The percutaneous catheter connection hub 28 and excess length of percutaneous catheter 20 are then cut off leaving about three inches of percutaneous catheter 20 protruding outside the patient. The proximal sleeve 44 with bushing 34 is then slid onto the percutaneous catheter 20 from the cut end. As described above for mounting a distal sleeve 30 with a bushing 34 on a percutaneous catheter 20, the proximal sleeve 44 with bushing 34 can similarly be mounted on a percutaneous catheter 20. Namely, reference is made to FIGS. 4, 5, 6A and 6B, and accompanying disclosures above regarding close fit (see, FIG. 5), flange 40 (see, FIG. 5) and diaphragm 42 (see, FIGS. 6A and 6B). All of these embodiments provide fluid tight seals against percutaneous catheter 20 without excessive friction so assembly is facilitated.

Finally, with the percutaneous catheter 20 inserted in the patient and the proximal sleeve 44 mounted on the percutaneous catheter 20, a retaining plate 46 is positioned with the percutaneous catheter 20 in the plate opening 48 using the cut 54. So configured the retaining plate 46 is moved to have the bushing 34 abut against rim 50 with the proximal sleeve 44 passed through rim aperture 52. Now the retaining plate 46 is adhered to the patient's skin 26 and the bushing 34 abutting the rim 50 restrains withdrawal of the percutaneous catheter 20 from the patient.

Figure 17:
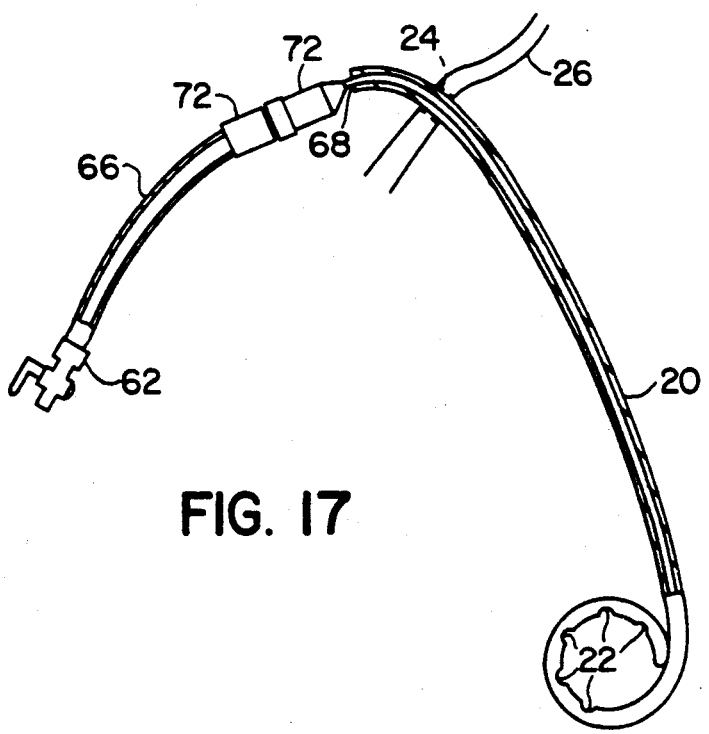
FIG. 17 is a plan partial sectional view of a fourth embodiment of the catheter apparatus of the present invention showing use of a curved blunt needle.

A fourth embodiment of the catheter apparatus 10 of the present invention uses a curved blunt needle 64 and proximal tube 66 instead of either a distal sleeve 30 or proximal sleeve 44 (see, FIG. 17). As with prior embodiments, this fourth embodiment can also be used either as the initial catheter retention system or as a repair kit for an externally damaged percutaneous catheter. Unlike prior embodiments, though, the fourth embodiment uses a curved blunt needle 64. Straight blunt tip needles are known for use with ureteral stents where they are inserted into the end of stents to help connect the stents to drainage bags. A supplier of straight blunt needles is Monoject, a division of Sherwood Medical, St. Louis, MO. For the present invention the blunt needle has a curved shank 68. As a further modification, the curved blunt needle 64 can also include retention ridges 70 on the curved shank 68. The purpose of the retention ridges 70 is explained below.

Using standard techniques, such as described above, a percutaneous catheter 20 is placed in a patient through a catheter entry site 24. The percutaneous catheter connection hub 28 and excess length of percutaneous catheter are then cut off leaving only a short section of percutaneous catheter 20 protruding outside the patient. Now the curved blunt needle 64 is inserted into the lumen of the percutaneous catheter 20. The fit between the curved shank 68 and the percutaneous catheter 20 lumen needs to be tight enough to provide a fluid tight seal. Such sealing can be expedited by the retention ridges 70 described above. Depending on need, a clamp (not shown) may optionally be fitted at the junction of the curved blunt needle 64 and the percutaneous catheter 20 to ensure a fluid tight seal.

With the curved blunt needle 64 inserted in the percutaneous catheter 20 there is unavoidably provided a curved section for the percutaneous catheter 20 where it enters the patient thus prohibiting kinking. Now the tube hub 72 of the proximal tube 66 is connected to the needle hub 74 of curved blunt needle 64. As with the previous embodiments a retaining plate 46 is positioned adjacent the patient and using the cut 54 the percutaneous catheter 20 is positioned in the plate opening 48. So configured the retaining plate 46 is moved to have the tube hub 72 abut against rim 50 with the proximal tube 66 passed through rim aperture 52. Now the retaining plate 46 is adhered to the patient's skin 26 and the tube hub 72 abutting the rim 50 restrains withdrawal of the percutaneous catheter 20 from the patient.

The fifth embodiment of the catheter apparatus 10 of the present invention uses a distal inner telescoping sleeve 30 and a proximal outer telescope sleeve 76 preassembled with a percutaneous catheter 20 (see, FIGS. 18 and 19). Like the first embodiment the distal sleeve 30 is fitted with a bushing 34. Unlike prior described embodiments, this fifth embodiment is intended for application as part of initial use of the catheter retention system. But in conformity with all embodiments of the present invention, this fifth embodiment also provides for protection from damage of percutaneous catheters such as caused by kinking. This and other features are described below.

Using standard techniques, such as described above, a percutaneous catheter 20 is placed in a patient through a catheter entry site 24. However, unlike prior embodiments, before the percutaneous catheter 20 is placed in a patient, a string 78, which is tied to the proximal (second) end of a distal sleeve 30 opposite the bushing 34, is threaded through the proximal outer telescope sleeve 76. Then the combination of proximal outer telescope sleeve 76 with threaded string 78 and distal inner telescope sleeve 30 are slid onto the percutaneous catheter 20 s the female threaded proximal outer telescope sleeve which is attached to the proximal (second) end of the proximal outer telescope sleeve 76, hub 80 can be brought adjacent the male threaded percutaneous catheter hub 82. As part of the procedure for assembly, the string 78, threaded through the proximal telescope tube 76, is also threaded through a hole in the male threaded section of the percutaneous catheter hub 82. This positioning of the string 78 through and adjacent the threads of the percutaneous catheter hub 82 provides a portion of a locking system for the string 78 when the female threaded proximal tube hub 80 is mated to the percutaneous catheter hub 82 and the string 78 is compressed between the tightened threads. These arrangements for the percutaneous catheter 20, distal inner telescoping sleeve 30, proximal outer telescope tube 76, string 78, proximal tube hub 80 and percutaneous catheter hub 82 are shown in FIGS. 18 and 19. The arrangement of components is shown over extended in FIG. 18 for clarity and fully contracted in FIG. 19.

Using the configuration for the fifth embodiment as shown in FIG. 19, but with the male threaded percutaneous catheter hub 82 unthreaded sufficiently from the female threaded proximal tube hub 80 that the string 78 is not locked in a single position, the percutaneous catheter 20 is inserted into a patient. Now the distal inner telescope sleeve 30 is extended down the percutaneous catheter 20 so the bushing 34 is adjacent the entry point of the percutaneous catheter 20 into the patient. With this configuration of the percutaneous catheter 20, distal inner telescope sleeve 30 and proximal outer telescope sleeve 76 the string 78 is locked in position by tightening proximal outer telescope sleeve hub 80 onto percutaneous catheter hub 82.

Finally, a retaining plate 46 is positioned with the percutaneous catheter 20 in the plate opening 48 using the cut 54. So configured the retaining plate 46 is moved to have the bushing 34 abut against rim 50 with the distal sleeve 30 passed through rim aperture 52. Now the retaining plate 46 is adhered to the patient's skin 26 and the bushing 34 abutting the rim 50 restrains withdrawal of the percutaneous catheter 20 from the patient.

Both the distal sleeve 30 and the proximal telescope tube 76 are made of supple tubing material and are of sufficient length that the percutaneous catheter 20 is sheathed and therefore protected from damage including kinking damage.

Figure 22:
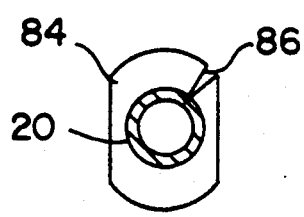
FIG. 22 is a front plan view of a retention clamp of the present invention with a section of the percutaneous catheter of FIG. 21 taken along line 22—22.
Figure 20:
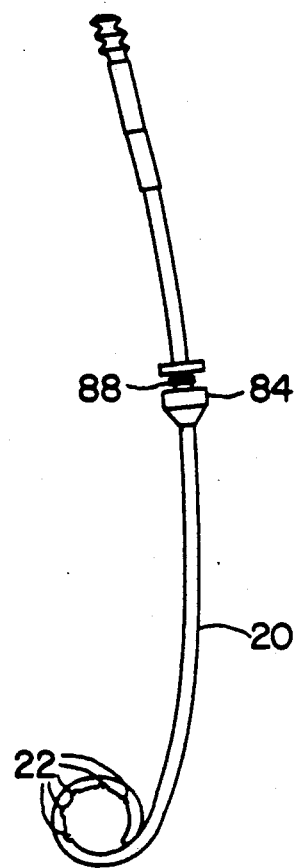
FIG. 20 is a plan view of a percutaneous catheter with a retention clamp of the present invention.
Figure 21:
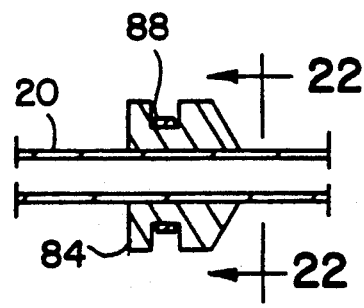
FIG. 21 is a sectional view of a retention clamp of the present invention on a percutaneous catheter.

A sixth embodiment includes a retention clamp 84 as shown in FIGS. 20, 21 and 22 can be used instead of bushings 34, or distal sleeve hubs 36 and 38 for abutment against rim 50. The clamp 84 is unique in that it is sized to form a flush profile with the top surface of rim 50.

Using standard techniques, such as described above, a percutaneous catheter 20 is placed in a patient through a catheter entry site 24. A retention clamp 84 can then be fitted around the percutaneous catheter 20 at a position next to the point of entry into the patient of the percutaneous catheter 20. Such fitting of a retention clamp 84 is feasible because of a cut 86 to the central bore of the retention clamp 84. After the retention clamp 84 is properly positioned on the percutaneous catheter 20 a band 88 is tightly affixed about the retention clamp 84 to firmly maintain the position of the retention clamp 84 on the percutaneous catheter 20. A retaining plate 46 is now positioned with the percutaneous catheter 20 in the plate opening 48 using the cut 54. So configured the retaining plate 46 is moved to have the retention clamp 84 abut against rim 50 with the percutaneous catheter 20 passed through rim aperture 52. Now the retaining plate 46 is adhered to the patient's skin 26 and the retention clamp 84 abutting the rim 50 restrains withdrawal of the percutaneous catheter 20 from the patient. Further the length of the retention clamp 84 may be sufficient to prevent inward migration of the percutaneous catheter 20 which is also precluded since the retention clamp 84 is too big to enter the catheter entry site 24.

Use of the retention clamp 84 of the present invention avoids using sutures or adhesives applied to the percutaneous catheter 20. Therefore, replacement of the retaining plate 46 is a simple and quick process.

If retention clamp 84 is initially used with only a percutaneous catheter 20 and the percutaneous catheter 20 is damaged then the retention clamp 84 can be removed and any of the first through fourth embodiments of the present invention could be used as described above.

The above discussion and related illustrations of the present invention are directed primarily to preferred embodiments and practices of the invention. However, it is believed numerous changes and modifications in the actual implementation of the concepts described above will be apparent to those skilled in the art, and it is contemplated that such changes and modifications may be made without departing from the scope of the invention as defined by the following claims.

What is claimed is:

1. A catheter device comprising:
a percutaneous catheter tube having a distal portion for insertion into the body of a patient;
a distal sleeve means having a bushing means at a first end so said distal sleeve means can be slid onto said percutaneous catheter tube and wherein said bushing means is moved adjacent the skin where said catheter tube enters into said patient; and
a proximal sleeve means having a first attachment means at one end so said proximal sleeve means can be slid onto said percutaneous catheter tube which extends beyond a second end of said distal sleeve means, said first attachment means being joined to a second attachment means at a second end of said distal sleeve means, and said joined first attachment means and said second attachment means providing a fluid tight seal about said catheter tube.

2. A catheter device according to claim 1 in which a retaining means is attached to the skin of said patient and said bushing means is brought in contact with said retaining means.

3. A catheter device according to claim 1 in which said first attachment means includes a male threaded portion.

4. A catheter device according to claim 3 in which said second attachment means includes a female threaded portion.

5. A catheter device according to claim 1 in which said first attachment means includes a female threaded portion.

6. A catheter device according to claim 5 in which said second attachment means includes a male threaded portion.

7. A catheter device according to claim 1 in which said fluid tight seal is provided by a washer means.

8. A catheter device according to claim 1 in which said bushing means includes a flange means for providing a second fluid tight seal about said percutaneous catheter tube.

9. A catheter device according to claim 1 in which said bushing means includes a diaphragm means for providing a second fluid tight seal about said percutaneous catheter tube.

10. A method for catheterization including the steps of:
inserting a percutaneous catheter tube in a patient;
sliding a distal sleeve means having a bushing means onto said percutaneous catheter tube so said bushing means is adjacent the skin of said patient;
sliding a proximal sleeve means having a first attachment means onto said percutaneous catheter tube, and joining said first attachment means to a second attachment means joined to said distal sleeve means to provide a fluid tight seal about said percutaneous catheter tube.

11. A method of catheterization according to claim 10 including the step of positioning said bushing means so as to be in restrained contact with a retaining means attached to said skin of said patient.

* * * * *